(12) United States Patent
Harrah et al.

(10) Patent No.: US 9,801,651 B2
(45) Date of Patent: Oct. 31, 2017

(54) TISSUE EXTRACTION DEVICES AND RELATED METHODS

(71) Applicant: Boston Scientific Scimed, Inc., Maple Grove, MN (US)

(72) Inventors: Timothy Harrah, Cambridge, MA (US); Jozef Slanda, Milford, MA (US); Jianmin Li, Lexington, MA (US); Prateet Verma, Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 85 days.

(21) Appl. No.: 14/692,926

(22) Filed: Apr. 22, 2015

(65) Prior Publication Data

US 2015/0305768 A1    Oct. 29, 2015

Related U.S. Application Data

(60) Provisional application No. 61/983,159, filed on Apr. 23, 2014.

(51) Int. Cl.
| | | |
|---|---|---|
| *A61B 17/3205* | (2006.01) | |
| *A61B 17/221* | (2006.01) | |
| *A61B 17/00* | (2006.01) | |

(52) U.S. Cl.
CPC ...... *A61B 17/32056* (2013.01); *A61B 17/221* (2013.01); *A61B 2017/00353* (2013.01)

(58) Field of Classification Search
CPC ............ A61B 17/221; A61B 17/32056; A61B 17/32075; A61B 17/3207; A61B 2017/00358; A61B 2017/320733; A61B 2017/00353; A61B 2017/2212

USPC .......................... 606/113, 114, 127, 128, 159
See application file for complete search history.

(56) References Cited

U.S. PATENT DOCUMENTS

| | | | |
|---|---|---|---|
| 6,024,751 A | 2/2000 | Lovato et al. | |
| 6,174,318 B1 * | 1/2001 | Bates | A61B 17/221 606/113 |
| 6,652,548 B2 | 11/2003 | Evans et al. | |
| 2008/0033467 A1 * | 2/2008 | Miyamoto | A61B 17/22 606/180 |
| 2009/0060977 A1 | 3/2009 | Lamson et al. | |
| 2010/0106238 A1 * | 4/2010 | Hilaire | A61F 2/954 623/1.11 |
| 2013/0006262 A1 * | 1/2013 | Lampropoulos | A61B 17/221 606/113 |
| 2013/0041359 A1 * | 2/2013 | Asselin | A61B 17/32053 606/27 |

(Continued)

*Primary Examiner* — Katrina Stransky
(74) *Attorney, Agent, or Firm* — Bookoff McAndrews, PLLC (57) ABSTRACT

According to one aspect, a medical device may include a luminal element configured for insertion into a natural body lumen. The medical device may further include a tool configured to be received within the luminal element. The tool may include a plurality of operating members. Each of the operating members may include an elongate member and a cutting member. The cutting member may be located at a distal end of the elongate member. Further, the cutting member of a first operating member of the plurality of operating members may be rotatable with respect to the cutting member of a second operating member of the plurality of operating members.

20 Claims, 6 Drawing Sheets

(56) References Cited

U.S. PATENT DOCUMENTS

2013/0131688 A1\* 5/2013 Schwartz ............ A61B 17/221
606/113

\* cited by examiner

TISSUE EXTRACTION DEVICES AND RELATED METHODS

CROSS REFERENCE TO RELATED APPLICATIONS

This application claims the benefit of U.S. Provisional Application No. 61/983,159, filed Apr. 23, 2014, the disclosure of which is incorporated herein by reference in its entirety.

DESCRIPTION OF THE DISCLOSURE

Field of the Disclosure

Embodiments of the present disclosure relate generally to medical devices and procedures. In particular, embodiments of the present disclosure relate to medical devices and methods for tissue extraction.

Background of the Disclosure

Benign Prostatic Hyperplasia (BPH) is noncancerous enlargement of the prostate gland in men. BPH includes hyperplasia (an increase in the number of cells) of prostatic stromal and epithelial cells which result in the formation of large nodules in the periurethral region of the prostate. As the prostate enlarges it puts pressure on and/or partially or completely occludes the urethra. Additionally, prostate enlargement may cause pain, difficulty in urination, infection, or the like.

Enucleation of the Prostate (EP) is a technique for treating BPH. EP typically involves inserting an energy (e.g., laser) device into the urethra and directing the device to a target tissue including enlarged prostate tissue. Typically, such laser devices are directed to the target tissue using a sheath such as, for example, a cystoscope and/or rectoscope. The laser device enucleates (e.g., separates or removes) the target prostate tissue away from its surroundings. Typically the separated prostate tissue may form one or more large pieces of tissue, referred to as "tissue balls", which are then directed (e.g., pushed) into the bladder using the laser device or another medical device. While referred to herein as a "ball," the severed tissue may not necessarily be in the shape of a ball (e.g., sphere) but rather, may have any shape including irregular shapes. The laser device is then removed and another device such as a morcellator is introduced into the sheath for removing the tissue. A morcellator is a surgical device having a small opening at its distal end, one or more cutting blades, and suction capability. The blades may cut (e.g., mince, puree) the large pieces of tissue, e.g., tissue balls, that were moved into the bladder into smaller pieces. These smaller pieces may then be removed out of the body through the opening via, suction and/or other means.

There are, however, disadvantages to using conventional methods for removing tissue balls. For example, due to its small opening at the distal end, the morcellator may require a significant amount of time to cut the larger pieces of tissue into smaller ones for removal from the body. Moreover, since the morcellator includes one or more moving blades, there is a risk of damaging surrounding tissue. Accordingly, it may be desirable to provide for alternative systems and methods for tissue extraction.

SUMMARY OF THE DISCLOSURE

Aspects of the present disclosure include a medical device, such as a tissue extractor, that may be used to remove excised tissue from a body and methods of use thereof.

In one example, a medical device may comprise a luminal element configured for insertion into a natural body lumen. The medical device may further include a tool configured to be received within the luminal element. The tool may include a plurality of operating members, each of the operating members including an elongate member and a cutting member. The cutting member may be located at a distal end of the elongate member. Further, the cutting member of a first operating member of the plurality of operating members may be rotatable with respect to the cutting member of a second operating member of the plurality of operating members.

The medical device may further include one or more of the following features: the cutting member of each of the plurality of operating members may include a loop of wire; a cross-sectional shape of the loop of wire of each of the cutting members of the plurality of operating members may include at least one of a circular, square, rectangular, oval, diamond, and triangular shape; the loop of wire of each of the cutting members of the plurality of operating members may include at least one of nitinol and stainless steel; the luminal element may include a tapered distal end portion; the tool may be configured to transition between a receiving configuration and a trapping configuration, when in the receiving configuration, the cutting member of the first operating member may be configured to nest within the cutting member of the second operating member so as to define a receiving space within the cutting members of the first and second operating members, and when in the trapping configuration, the cutting member of the first operating member may be configured to rotate relative to the cutting member of the second operating member so as to form a trap configured to retain material therein; the tool may be axially translatable relative to the luminal element; when in the trapping configuration, the cutting member of the first operating member may be configured to rotate about 90° relative to the second operating member; the plurality of operating members may include at least four operating members; the plurality of operating members may include at least six operating members; the plurality of operating members may include at least eight operating members; at least one cutting member of the plurality of operating members may be independently rotatable with respect to at least another cutting member of the plurality of operating members; each of the cutting members of the plurality of operating members may be independently rotatable with respect to each other cutting member of the plurality of operating members; a retention member may be configured to retain the elongate member of each operating member therein; and the retention member may include one or more of a clip, a bracket, a band, a strap, and a luminal member.

In an additional or alternative example, a method of extracting tissue may include advancing a luminal element into a natural body lumen. The method may further include advancing a tool through the luminal element. The tool may include a plurality of operating members and each of the operating members may include an elongate member and a cutting member. The cutting member may be located at a distal end of the elongate member. The method may further include surrounding target tissue within the cutting members of each of the operating members. Additionally, the method may include rotating the cutting member of a first operating member of the plurality of operating members relative to the cutting member of a second operating member of the plurality of operating members to trap the target tissue therein. Also, the method may include retracting the cutting members of the first and second operating members into the luminal element so as to cut the target tissue.

The method may further include one or more of the following features: the cutting member of each of the plurality of operating members may include a loop of wire; a cross-sectional shape of the loop of wire of each of the cutting members of the plurality of operating members may include at least one of a circular, square, rectangular, oval, diamond, and triangular shape; the loop of wire of each of the cutting members of the plurality of operating members may include at least one of nitinol and stainless steel; removing the cut target tissue via a lumen of the luminal element; advancing a grasping member through the luminal element; coupling the luminal element to a source of suction; and wherein at least one cutting member of the plurality of operating members may be independently rotatable with respect to at least another cutting member of the plurality of operating members.

In an additional or alternative example, a method of extracting tissue may include advancing a luminal element into a natural body lumen. The method may further include advancing a tool through the luminal element. The tool may include a plurality of independently actuatable operating members. Each of the operating members may include an elongate member and a cutting member. The cutting member may be located at a distal end of the elongate member. The method may further include surrounding target tissue within the cutting members of each of the operating members and rotating the cutting member of a first operating member of the plurality of operating members relative to the cutting member of a second operating member of the plurality of operating members to trap the target tissue therein. The method may further include retracting the cutting members of the first and second operating members into the luminal element so as to cut the target tissue, and removing the cut target tissue via a lumen of the luminal element.

Additional objects and advantages of the present disclosure will be set forth in part in the description which follows, and in part will be understood from the description, or may be learned by practice of the claimed disclosure. The objects and advantages of the claimed disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts. As used herein, the term "distal" refers to the direction that is away from the user and into the patient's body. By contrast, the term "proximal" refers to the direction that is closer to the user and away from the patient's body.

Overview

Embodiments of the present disclosure may include a medical device for removing and/or retrieving a material from a body and methods of use thereof. In some embodiments, the medical device may be used to retrieve tissue that has been cut away or otherwise severed from its surroundings. In at least one embodiment, the tissue to be removed may be tissue from the prostate for treatment of BPH. In alternative embodiments, the medical device may be used to remove other types of tissues or materials such as, for example, bladder stones, kidney stones, and the like. For convenience, the exemplary medical device discussed herein is referred to as an extraction device; however, this reference is merely made for convenience, and is intended to include devices capable of other and/or additional operations and/or functions such as resection.

In the following sections, embodiments of the present disclosure will be described using the bladder as an exemplary body organ. It will be understood that the bladder is merely an example and that the device may be utilized in other parts of the body, for example the uterus or the intestines.

The present disclosure provides medical devices for removing tissue from a patient's body, such as, tissue extraction devices. The medical devices may be used to remove tissue that has been cut away or excised from the body. An opening or working channel of the extraction device may facilitate removal of excised tissue from the body. The extraction device may be configured to be introduced into the body through a suitable natural opening, such as through the urethra.

EXEMPLARY EMBODIMENTS

Figure 1:
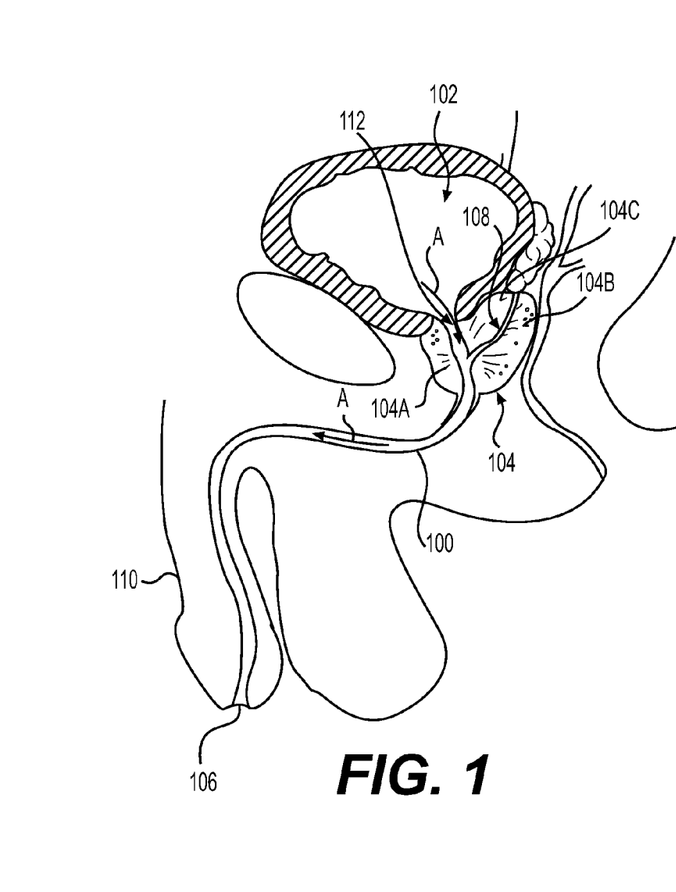
FIG. 1 illustrates a male pelvic region with a healthy urinary system.

FIG. 1 illustrates the pelvic region of a male having a healthy urinary system. As shown in FIG. 1, the urinary system includes a urethra 100, a bladder 102, a prostate 104, a urinary meatus 106, and an ejaculatory duct 108 of the male urinary system. The urethra 100 is a biological lumen connecting bladder 102 to the urinary meatus 106 at the tip of the penis 110. The urethra 100 connects to the bladder 102 at bladder opening 112. As shown, the prostate 104 is positioned around the urethra 100 between the bladder 102 and the penis 110. Upon stimulation, the bladder 102 constricts and urine (depicted by arrow A) is released out of the urinary meatus 106 through the urethra 100.

Figure 2:
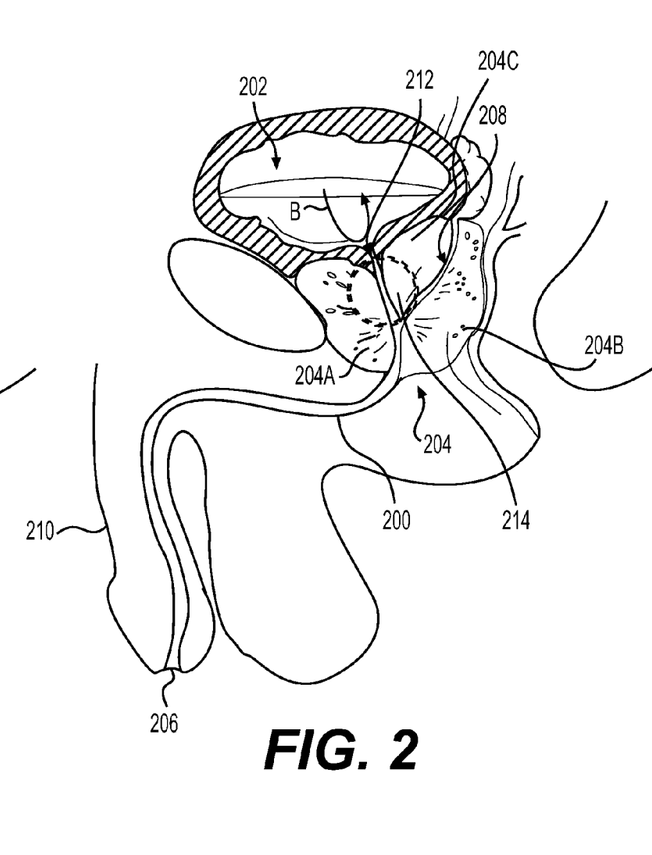
FIG. 2 illustrates a male pelvic region suffering from Benign Prostatic Hyperplasia (BPH)

FIG. 2 illustrates the male pelvic region suffering from Benign Prostate Hyperplasia (BPH). As shown, the pelvic region includes a urethra 200, a bladder 202, a prostate 204, a urinary meatus 206, an ejaculatory duct 208, a penis 210, and a bladder opening 212. In BPH, the passage of urine through the urethra 200 from the bladder 202 to the urinary meatus 206 at the tip of the penis 210 is obstructed by the enlarged prostate 204. For example, an excess tissue region 214 in the enlarged prostate 204 may constrict (e.g., narrow, obstruct, and/or partially occlude) the urethra 200 proximate to the bladder opening 212, and may cause pain, difficulty in urination, and/or urinary infections. For example, due to constriction of the urethra, urine (depicted by arrow B) is prevented from freely flowing through the urethra 200 to exit the penis 210 via the urinary meatus 206. In turn, it may result in urine buildup in the bladder 202. This accumulation of urine may increase infection and the occurrence of other urinary tract problems. In addition, the enlarged prostate 204 may constrict (e.g., narrow, obstruct, and/or partially occlude) the ejaculatory duct 208 causing erectile dysfunction or ejaculatory problems.

The enlarged prostate 204 may be severed using various methods, such as, laser enucleation as is known in the art. In laser enucleation, a laser is used to cut (e.g., sever, ablate) tissue from remaining portions of the enlarged prostate 204. By way of example only, laser enucleation may be used to cut excess tissue region 214 from the enlarged prostate 204 in order to alleviate constriction of the urethra 200. Cutting or severing of such tissue may form a tissue ball. Once formed, the tissue ball may be moved (e.g., pushed) into the bladder 202 for removal via an appropriate tool. The tissue ball is undesirable and may be removed by using a morcellating tool to cut the tissue ball into small pieces. Due to its small opening at the distal end, the morcellator may require a significant amount of time to cut the larger pieces of tissue into smaller ones for removal from the body. Moreover, since the morcellator includes one or more moving blades, there is a risk of damaging surrounding tissue. The embodiments of the medical device discussed below provide for efficient removal of tissue balls while preventing damage to surrounding tissue.

Figures 3A, 3C:
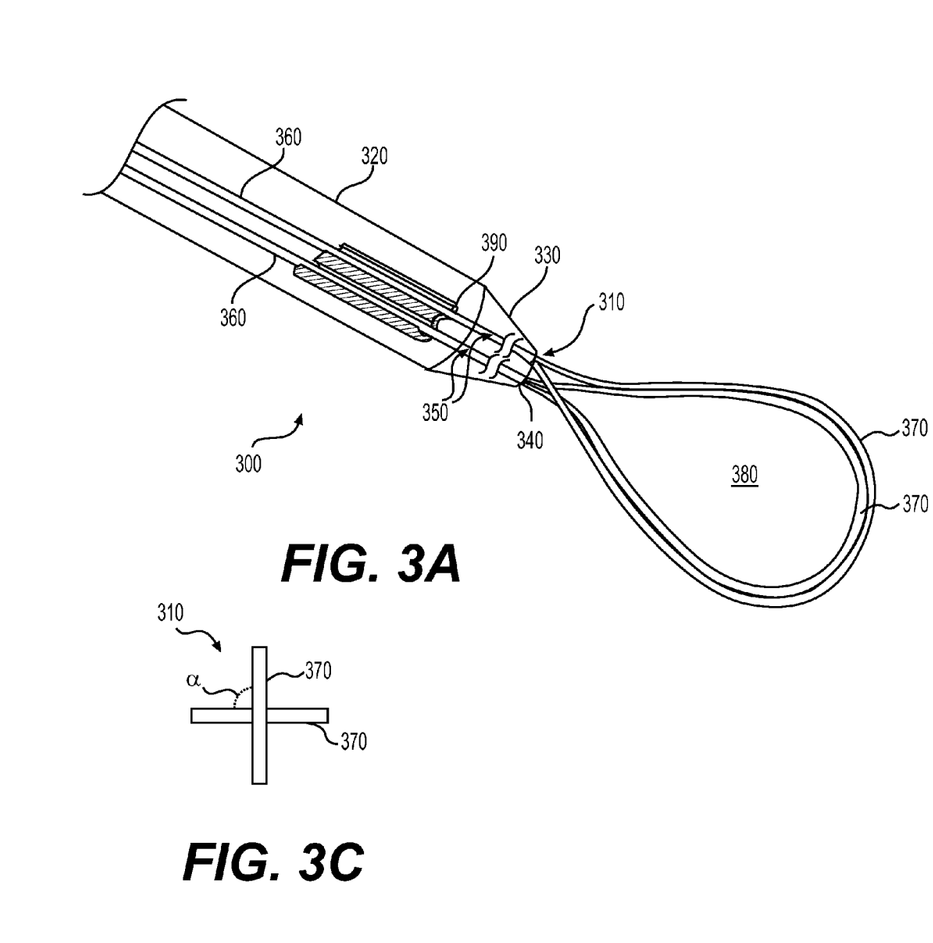
FIG. 3A illustrates an exemplary medical device, according to an embodiment of the present disclosure.
FIG. 3C illustrates a distal end view of the exemplary medical device of FIG. 3A in a trapping configuration.

FIG. 3A illustrates an exemplary medical device 300 that may be used to remove large pieces of severed tissue, e.g., tissue balls, from a body cavity, according to the present disclosure. The medical device 300 may include a tool (e.g., working member) 310 which may be received within a lumen (e.g., working channel) of an elongate luminal element 320 (e.g., sheath, introducer, scope device). For example, tool 310 may have an outer dimension (e.g., diameter) smaller the a diameter of the lumen of an appropriate elongate luminal element 320 such that tool 310 is axially translatable relative to the elongate luminal element 320. Accordingly, tool 310 may be readily inserted into a body via the elongate luminal element 320. It is understood that elongate luminal element 320 may include a plurality of lumens extending therethrough such that additional working members 310 and/or other tools may be introduced into a patient.

Figure 12:
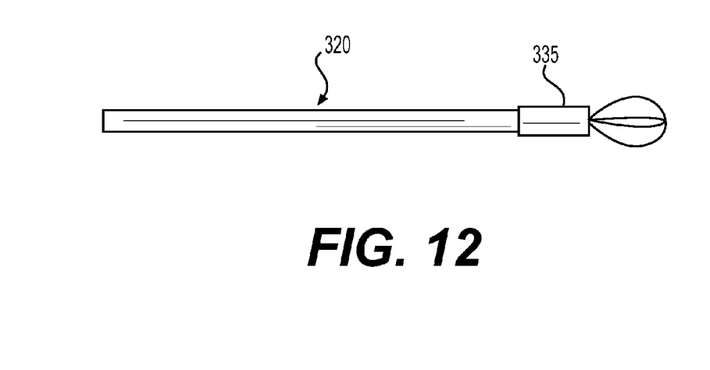
FIG. 12 illustrates an alternative elongate luminal element according to a further embodiment of the present disclosure.

Additionally, the tool 310 and/or a lumen of the elongate luminal element 320 may be coated with or comprised of a lubricious material to facilitate smooth insertion of the tool 310 through the lumen of the elongate luminal element 320. The elongate luminal element 320 may have any cross-sectional shape configured for insertion into a natural body lumen (e.g., urethra) of a patient. For example, the elongate luminal element 320 may have a circular, oval, or irregular cross-sectional shape. It is understood that the elongate luminal element 320 may have additional or alternative cross-sectional shapes without departing from the scope of this disclosure. Additionally, it is understood that the cross-sectional shape of the elongate luminal element 320 may change along the length of the elongate luminal element 320. For example, elongate luminal element 320 may include a tapered distal end portion 330. Tapered distal end portion 330 may comprise a narrowing or reduced profile portion of elongate luminal element 320. Tapered distal end portion 330 may facilitate insertion of elongate luminal element 320 a natural body lumen. Further, tapered distal end portion 330 may include a sharpened end face 340 configured to facilitate cutting target tissue as will be explained in further detail below. Alternatively, as shown in FIG. 12, elongate luminal element 320 may include a flat distal end portion 335. Flat distal end portion 335 may be easier and less expensive to manufacture.

The tool 310 may include a plurality of operating members 350. For example, as shown in FIG. 3A, the tool 310 may include at least two operating members 350. While only two operating members 350 are shown, it is understood that any number of operating members 350 may be used without departing from the scope of this disclosure. For example, the tool 310 may include between 2 and 12 operating members 350 depending on the intended application of the tool 310. For example, as discussed in further detail below, additional operating members 350 may be used so as to cut target tissue into smaller pieces while fewer operating members 350 may be used so as to cut target tissue into larger pieces. Further, the number of operating members 350 may be selected on the basis of the target tissue type. For example, for harder tissue types (e.g., stones, calcified tissue, fibrous tissue, and scar tissue), a medical professional may determine a fewer number of operating members 350 may be more effective to cut through the target tissue.

Each operating member 350 may include an elongate member 360 and a cutting member 370 (e.g., basket member). A proximal end of each elongate member 360 may extend to a proximal end of the elongate luminal element 320 for manipulation or actuation by a medical professional as will be described in further detail below. Accordingly, each elongate member 360 may be comprised of a material having sufficient columnar and torsional strength or stiffness for manipulation by a medical professional. Cutting member 370 may be located at a distal end of elongate member 360. For example, elongate member 360 and cutting member 370 may be monolithically formed so as to comprise a continuous one-piece construction. Alternatively, elongate member 360 may be coupled to cutting member 370 though any appropriate means (e.g., welding, chemical bonding, a mechanical joint, etc.).

As shown in FIG. 3A, the cutting member 370 of each operating member 350 may include a loop of wire (e.g., a snare loop). While referred to herein as a loop, the cutting members 370 may have any other shape appropriate for receiving target tissue therein. The loop of wire of the cutting member 370 may have a circular, oval, and/or polygonal shape. A cross-sectional shape of the loop of wire of the cutting members 370 may be at least one of a circular, square, rectangular, oval, diamond, and triangular shape. For example, in at least one embodiment, the cross-sectional shape of the loop of wire of the cutting members 370 may be diamond shaped. Such a cross-sectional shape may facilitate cutting target tissue as will be described in further detail below. Additionally, each loop of wire of the cutting members 370 may include a high-tensile strength drawn wire such as, for example, Nitinol™, stainless steel, and titanium alloys.

Figure 3B:
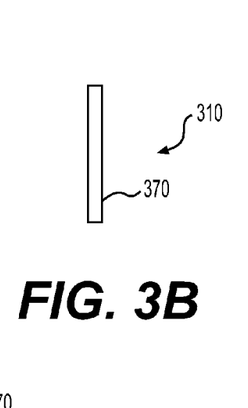
FIG. 3B illustrates a distal end view of the exemplary medical device of FIG. 3A in a receiving configuration.

The tool 310 may be configured to transition between a receiving configuration (FIGS. 3A, 5, 7, 8) and a trapping configuration (e.g., FIGS. 3C and 9-11). As shown in FIG. 3A, for example, in the receiving configuration, the cutting member 370 of a first operating member 350 may be configured to nest within (e.g., align, extend alongside) the cutting member 370 of a second operating member 350. For example, the loop of wire of each of the cutting members 370 may extend parallel to one another so as to define a receiving space 380. That is, the cutting members 370 may comprise complimentary shaped loops of wire so as to define receiving space 380. Accordingly, in the receiving configuration, a distal end view of the tool 310 may be substantially i-shaped as shown in FIG. 3B. It is understood that in some embodiments, the cutting members 370 may have different dimensions so as to facilitate nesting within one another. For example, a first cutting member 370 may have a smaller dimension or profile than a second cutting member 370 such that the outer dimension or profile of the first cutting member 370 may be substantially similar to the inner dimension or profile of the second cutting member 370.

In order to transition from the receiving configuration to the trapping configuration, at least one operating member 350 may be moved relative to another operating member 350. For example, at least a first operating member 350 may be rotatable with respect to a second operating member 350. For example, in an embodiment including two operating members 350, the first cutting member 370 may be configured to rotate an angle α (e.g., about 90°) relative to the second cutting member 370. As used herein, the terms about, substantially, and/or approximately mean within ±5%. Accordingly, in the trapping configuration, a distal end view of the tool 310 may be substantially cross-shaped as shown in FIG. 3C. In the trapping configuration, the cutting members 370 form a whisk-shaped cage to trap target tissue in, as will be described in further detail below.

It is understood, however, angle α may be any angle between 0° and 180°. In an embodiment including, for example, three operating members 350, the cutting members 370 may be rotated such that they are spaced approximately 30° apart from one another. It is noted that the spacing between the cutting members need not be equidistant. For example, in at least some embodiments, the angle α (e.g., spacing) between two adjacent cutting members 370 may be different than the angle α (e.g., spacing) between two other adjacent cutting members 370. The angle α may be selected based on a number of factors including, for example, the number of operating members 350 within the tool 310, the desired space between each cutting member 370, the desired size of cut target tissue portions, the desired number of cut target tissue portions, etc.

The cutting members 370 may be moved (e.g., rotated) via any appropriate means. For example, cutting members 370 may be moved via manual manipulation by a medical professional and/or mechanical power (e.g., a motor). The elongate member 360 coupled to or monolithically formed with each cutting member 370 extends to a proximal end of the elongate luminal element 320. The medical professional may then manually move the proximal end of the elongate member 360, and therefore the cutting member 370, of a first operating member 350 relative to that of a second operating member 350. Alternatively, one or more of the elongate members 360 of the plurality of operating members 350 may be operably coupled to a mechanical power source (e.g., motor) through any appropriate means (e.g., linkages, gears, etc.) such that once powered, the elongate member 360, and therefore the cutting member 370, of a first operating member 350 may be moved (e.g., rotated) relative to that of a second operating member 350. In at least some embodiments, at least one elongate member 360 and cutting member 370 of the plurality of operating members 350 is independently rotatable with respect to at least one other elongate member 360 and cutting member 370 of the plurality of operating members 350. In at least some other embodiments, each elongate member 360 and cutting member 370 of the plurality of operating members 350 is independently rotatable with respect to each other elongate member 360 and cutting member 370 of the plurality of operating members 350.

In order to prevent an operating member 350 from entangling, intertwining with, catching, and/or otherwise interfering with the remaining operating members 350, a retention member 390 may be disposed along the elongate members 360 of the plurality of operating members 350. For example, as shown in FIG. 3A, retention member 390 may include a support, e.g., a luminal element, having a plurality of lumens 395 (e.g., troughs, reception areas, guides, tracks). Each lumen 395 of the plurality of lumens 395 may be configured to receive a corresponding elongate member 350 of the plurality of operating members 350. For example, in an embodiment including two operating members, as shown in FIG. 3A, retention member 390 may include two lumens 395. It is understood, however, that more or less lumens 395 may be used depending on the number of operating members 350 in the tool 310. It is also understood, that while each lumen 395 of the retention member 390 is illustrated in FIG. 3A as receiving a single elongate member 360 of the operating member 350, each lumen 395 may be configured to receive a plurality of elongate members 360 of the plurality of operating members 350. Further, retention member 390 may be disposed anywhere along the length of the elongate members 360. For example, in at least one embodiment, the retention member 390 may be positioned proximate a distal end of the elongate members 360.

Figure 4:
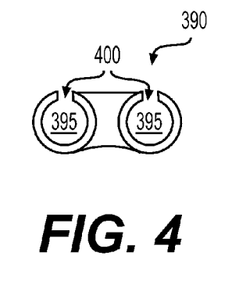
FIG. 4 illustrates the retention member of FIG. 3A.

As shown in FIG. 4, the lumens 395 of the retention member 390 may be c-shaped. For example, each lumen 395 may include a narrow elongate slot or opening 400 through which may be passed the elongate member(s) 360 of an operating member(s) 350. The width across the opening 400 may be smaller than a diameter or outer dimension of the elongate member 360. In such an embodiment, for example, the retention member 390 may be comprised of a semi-flexible and/or deformable material such that as an elongate member 360 is inserted through the opening 400, the retention member 390 may flex or expand such that a width across the opening 400 may be enlarged to receive the elongate member 360 therethrough. Once received within the lumen 395, the retention member 390 may return to its unstressed configuration in which the width across the opening 400 may return to its original narrow width and thereby retain the elongate member 360 within the lumen 395. It is understood that the illustrated configuration of retention member is exemplary only and that other arrangements are contemplated. For example, the retention member 390 may be devoid of openings 400. Rather, each lumen 395 may be defined by a tube and each elongate member 360 may be passed axially through the lumen 395. Additionally or alternatively, the retention member 390 may comprise one or more of a clip, a bracket, a band, and a strap. Additionally or alternatively, the elongate members 360 and/or the lumens 395 may be coated with or comprised of a lubricious material to facilitate smooth insertion of the elongate members 360 through the lumens 395 of the retention member 390.

Figures 5, 6:
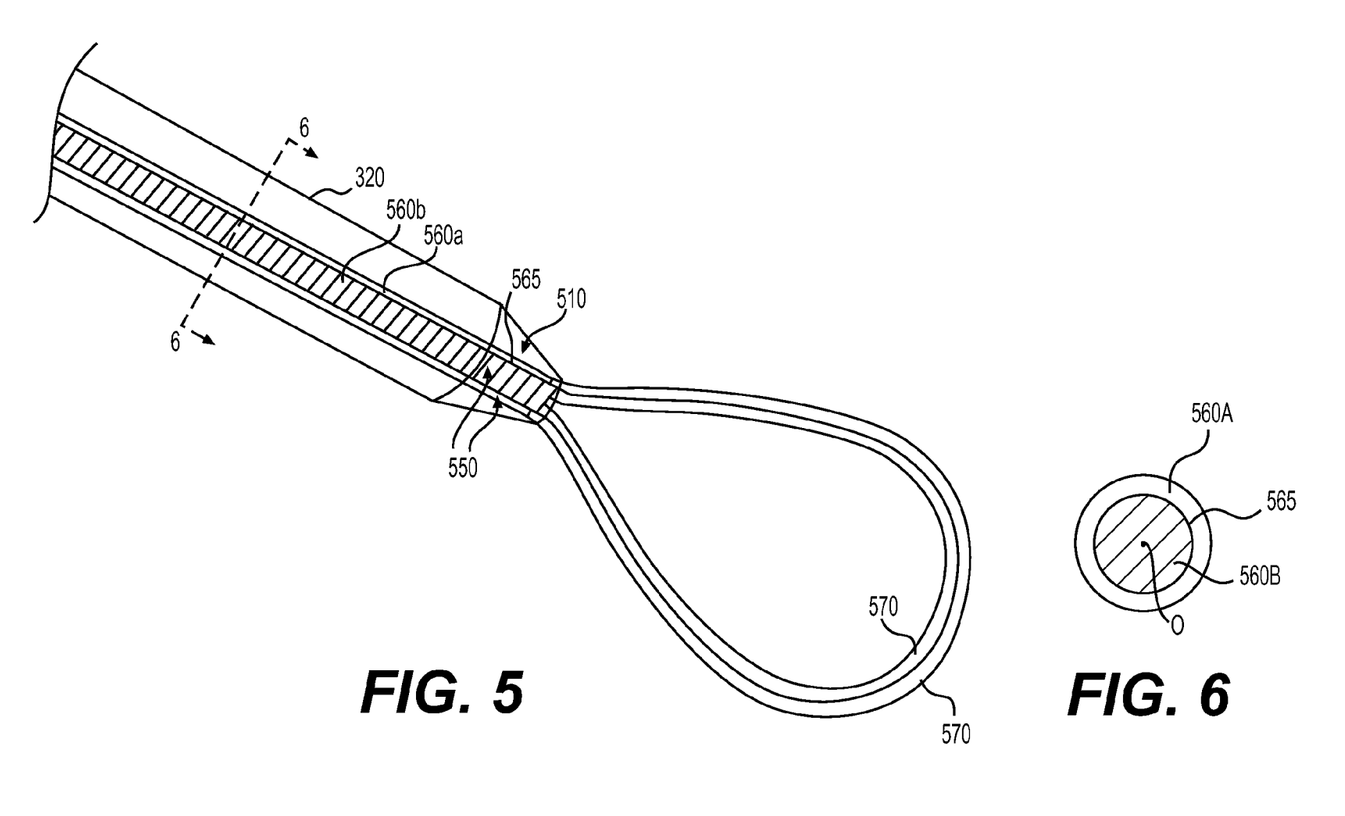
FIG. 5 illustrates an exemplary medical device, according to a further embodiment of the present disclosure.
FIG. 6 illustrates a cross-sectional view of the exemplary medical device of FIG. 5.

FIG. 5 depicts an alternative arrangement in which no retention member 390 is used. The embodiment illustrated in FIG. 5 includes similar features (e.g., cutting members 570, elongate luminal element 320, materials, configurations, etc.) to those of the embodiment illustrated in FIGS. 3A-3C with the exception of the design of the elongate members 560A, 560B. For example, as shown in FIG. 5, a working member 510 may include a plurality of operating members 550. For example, as shown in FIG. 5, the working member 510 may include at least two operating members 550. While only two operating members 550 are shown, it is understood that any number of operating members 550 may be used without departing from the scope of this disclosure. For example, the working member 510 may include between 2 and 12 operating members 550 depending on the intended application of the working member 510.

As shown in FIG. 5, each operating member 550 may include an elongate member 560A or 560B, and a cutting member 570. A proximal end of each elongate member 560 may extend to a proximal end of an elongate luminal element 320 for manipulation or actuation by a medical professional. A distal end of elongate member 560 may be coupled or monolithically formed with cutting member 570. For example, elongate member 560A, 560B and cutting member 570 may be monolithically formed so as to comprise a continuous one-piece construction. Alternatively, elongate member 560A, 560B may be coupled to cutting member 570 though any appropriate means (e.g., welding, chemical bonding, a mechanical joint, etc.).

In the embodiment illustrated in FIG. 5, elongate member 560A of a first operating member 550 may include a lumen 565 through which the elongate member 560B of a second operating member 550 may be received. That is, elongate member 560A may include a hollow passageway configured to receive elongate member 560B. FIG. 6 illustrates a cross-sectional view of elongate members 560A and 560B through plane 6-6. As shown, elongate members 560A and 560B may extend concentrically along a central axis O.

In order to transition from the receiving configuration to the trapping configuration, at least one operating member 550 may be moved relative to another operating member 550. For example, at least a first operating member 550 may be rotatable with respect to a second operating member 550. For example, in an embodiment including two operating members 550, the first cutting member 570 may be configured to rotate angle α (e.g., about 90°) relative to the second cutting member 570. In such an arrangement, elongate member 560B may rotate about axis O relative to and within elongate member 560A. Alternatively, elongate member 560A may rotate about axis O relative to and around elongate member 560B. Additionally or alternatively, the elongate members 560A and/or 560B may be coated with or comprised of a lubricious material to facilitate smooth rotation of one of elongate members 560A, 560B relative to the other.

Figure 7:
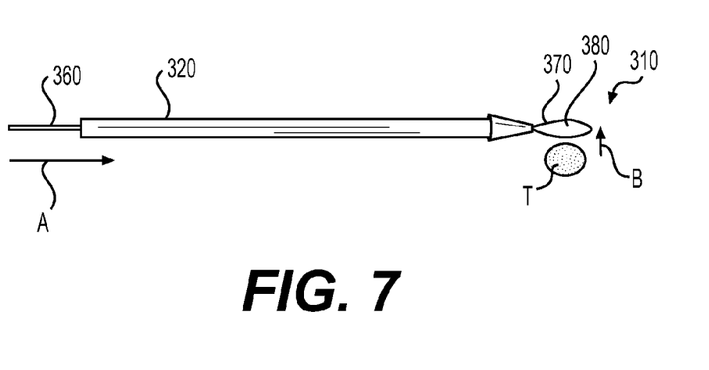
FIGS. 7-11 illustrate an exemplary method of extracting tissue according to a further embodiment of the present disclosure.

The following describes an exemplary method for removing excised tissue from a body according to the present disclosure. The method may be utilized for removing the excised tissue from patient's bladder, however, it is understood that the method may be utilized in other parts of the body. The elongate luminal element 320 may be introduced through the urethra of the patient and may be advanced toward the bladder. Once in position, the tool 310 may be advanced towards target tissue T in the direction A. It is understood, however, that in some embodiments, elongate luminal element 320 may be advanced toward the bladder while the tool 310 is positioned within the elongate luminal element 320. While tool 310, along with cutting member 370, elongate member 360, and operating member 350 are used to describe the exemplary method of FIGS. 7-11, it is understood that working member 510, along with cutting member 570, elongate member 560, and operating member 550 may also be used. As shown in FIG. 7, target tissue T may float freely in any direction, e.g., direction B within the patient's bladder. Upon advancing tool 310, the cutting member 370 may extend distally of the elongate luminal element 320.

Figure 8:
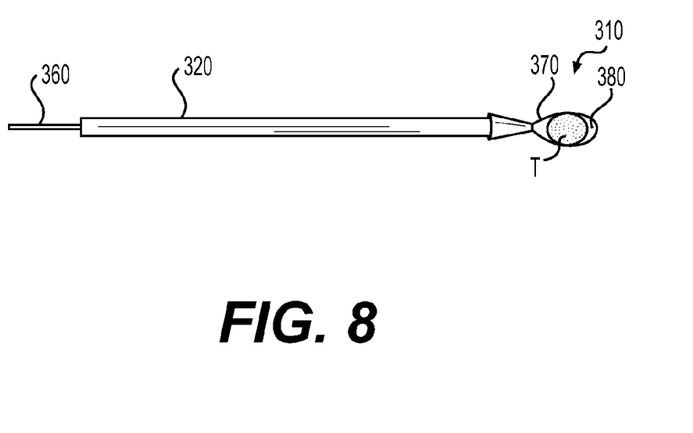
Figure 9:
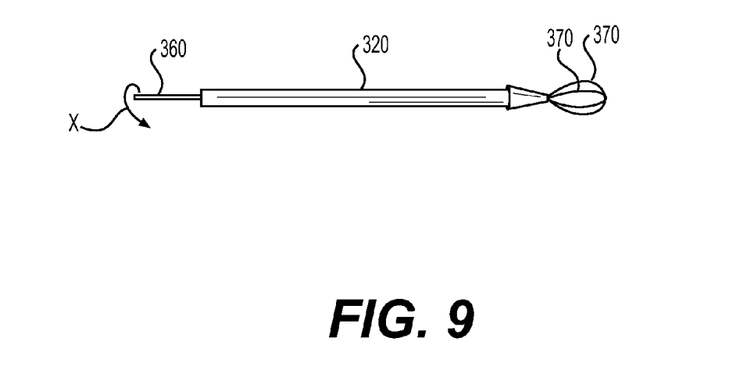
Figure 10:
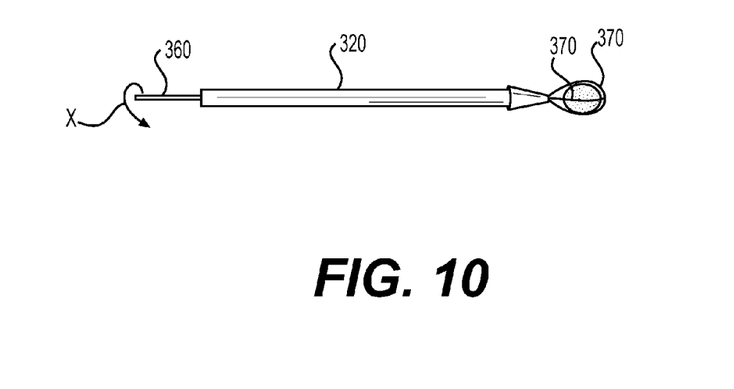

A medical professional may then manipulate the tool 310 so as to capture or surround the target tissue T within the receiving space 380 as shown in FIG. 8. For example, a medical professional may direct the cutting members 370 of the operating members 350, while in the receiving configuration (e.g., FIGS. 3A, 3B, 5, 7, and 8), to encircle the target tissue T. Once received within the receiving space 380, as shown in FIG. 8, a medical professional may then move at least one operating member 350 relative to another operating member 350. As such, the medical professional may cause the tool 310 to transition from the receiving configuration to the trapping configuration. For example, as shown in FIG. 9, in which the target tissue T has been removed for clarity, a medical professional may rotate the elongate member 360 of at least one operating member 350 in the direction X relative to another. Accordingly, the cutting member 370 of the at least one operating member 350 may rotate relative to the cutting member 370 of another cutting member so as to trap target tissue T therein as shown in FIG. 10.

Figure 11:
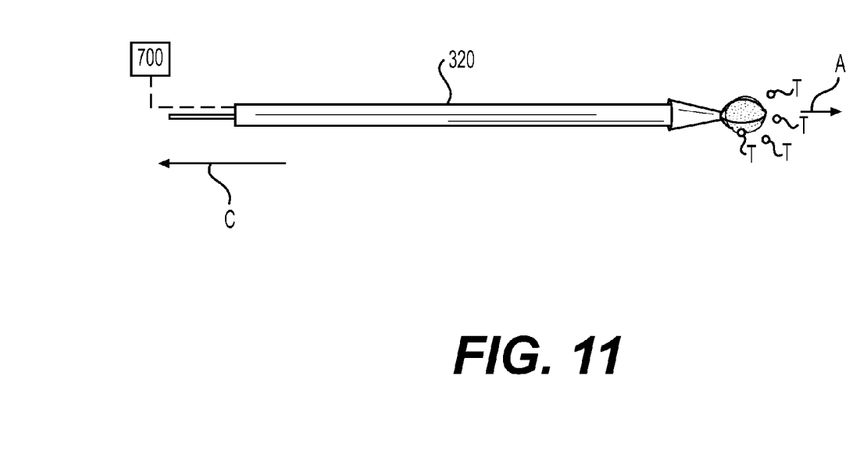

Once the target tissue T is retained within the working element 310 by virtue of the cutting members 370 in the trapping configuration, a medical professional may retract the working element 310 towards and into elongate luminal element 320. For example, a medical professional may pull elongate member(s) 360 or otherwise urge working element 310 to move in the direction of arrow C. As working element 310, including cutting members 370 are retracted within elongate luminal element 320, the target tissue is cut, sliced, or otherwise severed as cutting members 370 move through the target tissue T. Accordingly, the target tissue T is divided into smaller target tissue T portions.

Once the target tissue T is cut, a medical professional may then remove the cut target tissue via the lumen of the elongate luminal element 320. For example, removal device 700 such as, for example, a grasping member (not shown) may be advanced through a lumen of the elongate luminal element 320 and caused to grasp, pinch, grab, or otherwise secure the cut target tissue T portions therein. Once grasped, a medical professional may retract the grasping member proximally through the elongate luminal element 320 to remove the cut target tissue T portions. Alternatively, the removal device 700 may include a suction source and the elongate luminal element may be fluidly coupled with a source of suction or vacuum pressure (e.g., a vacuum pump) such that the target tissue T portions are drawn (e.g., sucked) into the elongate luminal element 320 and removed. It is understood that in some embodiments, tool 310 may be removed from elongate luminal element 320 prior to insertion of a grasper member or application of vacuum pressure. In other embodiments, however, tool 310 may be left within a first lumen of the elongate luminal element 320 while the grasper member is advanced through or a source of vacuum pressure is applied to a second lumen of the elongate luminal element 320.

Using the exemplary methods described above, the working element 310, 510 and elongate luminal element 320 may be used for extraction of resected tissue such as lesions from a patient's body for treatment or diagnostic purposes. The working element 310, 510 and elongate luminal element 320 may be a single-use devices which can be discarded after one use or may be used again after sterilization.

Other embodiments of the present disclosure will be apparent to those skilled in the art after consideration of the specification and practice of the embodiments disclosed herein. It is intended that the specification and examples be considered as exemplary only, with a true scope and spirit of the disclosure being indicated by the following claims.

What is claimed is:

1. A medical device, comprising:
   a luminal element;
      a tool movably received within the luminal element, the tool including a plurality of operating members, each of the operating members including a shaft and a cutting member, the cutting member being located at a distal end of the shaft;
      wherein the cutting member of a first operating member of the plurality of operating members is rotatable with respect to the cutting member of a second operating member of the plurality of operating members; and
      a multi-lumen retention clip positioned at a distal end of the luminal element.

2. The medical device of claim 1, wherein the cutting member of each of the plurality of operating members includes a loop of wire.

3. The medical device of claim 2, wherein a cross-sectional shape of the loop of wire of each of the cutting members of the plurality of operating members includes at least one of a circular, square, rectangular, oval, diamond, and triangular shape.

4. The medical device of claim 2, wherein the loop of wire of each of the cutting members of the plurality of operating members includes at least one of nitinol and stainless steel.

5. The medical device of claim 1, wherein the luminal element includes a tapered distal end portion.

6. The medical device of claim 1, wherein the tool is configured to transition between a receiving configuration and a trapping configuration, wherein in the receiving configuration, the cutting member of the first operating member is configured to nest within the cutting member of the second operating member so as to define a receiving space within the cutting members of the first and second operating members; and
   wherein in the trapping configuration, the cutting member of the first operating member is configured to rotate relative to the cutting member of the second operating member so as to form a trap configured to retain material therein.

7. The medical device of claim 6, wherein the tool is axially translatable relative to the luminal element.

8. The medical device of claim 6, wherein in the trapping configuration, the cutting member of the first operating member is positioned about 90° relative to the second operating member.

9. The medical device of claim 1, wherein the retention clip includes a plurality of c-shaped lumens extending therethrough.

10. The medical device of claim 1, wherein at least one cutting member of the plurality of operating members is independently rotatable and axially translatable with respect to at least another cutting member of the plurality of operating members.

11. A method of extracting tissue, comprising:
    advancing a luminal element into a natural body lumen;
    advancing a tool through the luminal element, the tool including a plurality of operating members, each of the operating members including a shaft and a cutting member;
    surrounding target tissue within the cutting members of each of the operating members;
    rotating the cutting member of a first operating member of the plurality of operating members relative to the cutting member of a second operating member of the plurality of operating members to trap the surrounded target tissue while rotating the shaft of the first operating member relative to a c-shaped lumen of a retention clip; and
    retracting the cutting members of the first and second operating members into the luminal element so as to cut the target tissue.

12. The method of claim 11, wherein the cutting member of each of the plurality of operating members includes a loop of wire.

13. The method of claim 12, wherein a cross-sectional shape of the loop of wire of each of the cutting members of the plurality of operating members includes at least one of a circular, square, rectangular, oval, diamond, and triangular shape.

14. The method of claim 12, wherein the loop of wire of each of the cutting members of the plurality of operating members includes at least one of nitinol and stainless steel.

15. The method of claim 11, further including:
    removing the cut target tissue via a lumen of the luminal element.

16. The method of claim 11, further including:
    advancing a grasping member through the luminal element.

17. The method of claim 15, further including:
    coupling the luminal element to a source of suction.

18. The method of claim 11, wherein at least one cutting member of the plurality of operating members is independently rotatable and axially translatable with respect to at least another cutting member of the plurality of operating members.

19. A method of extracting tissue, comprising:
    advancing a luminal element into a natural body lumen;
    advancing a tool through the luminal element, the tool including a plurality of independently actuatable operating members, each of the operating members including a shaft and a cutting member, the cutting member being located at a distal end of the shaft, and each shaft extending through a c-shaped lumen of a retention clip;
    surrounding target tissue within the cutting members of each of the operating members; and
    rotating the cutting member of a first operating member of the plurality of operating members relative to the cutting member of a second operating member of the plurality of operating members to trap the surrounded target tissue while rotating the shaft of the first operating member relative to a c-shaped lumen of a retention clip positioned at a distal end of the luminal element.

20. The method of claim 19, further including:
retracting the cutting members of the first and second operating members into the luminal element so as to cut the target tissue; and
removing the cut target tissue via a lumen of the luminal element.

\* \* \* \* \*